United States Patent [19]
Na et al.

[11] Patent Number: 6,099,845
[45] Date of Patent: Aug. 8, 2000

[54] **PROCESS FOR THE PREPARATION OF *RHUS VERNICIFLUA* EXTRACT AND ANTI-CANCER COMPOSITION CONTAINING SAME**

[75] Inventors: Chun-Soo Na; Nam-Chul Jung, both of Suwon; Eun-Sun Na, Yeocheon, all of Rep. of Korea

[73] Assignee: Forest Genetics Research Institute, Rep. of Korea

[21] Appl. No.: 09/063,853

[22] Filed: Apr. 21, 1998

[30] Foreign Application Priority Data

Aug. 1, 1997 [KR] Rep. of Korea ............. 97-3684

[51] Int. Cl.⁷ ............. A61K 35/78; A61K 35/385
[52] U.S. Cl. ............. 424/195.1
[58] Field of Search ............. 424/195.1

[56] References Cited

PUBLICATIONS

Nam et al., Nat. Prod. Sci., 2(2), 130–136 Abstract Only, 1996.
Kim et al., Int. J. Cosmet. Sci., 19(6), 299–307 Abstract Only, 1997.

*Primary Examiner*—Jerome D. Goldberg
*Attorney, Agent, or Firm*—Anderson Kill & Olick

[57] ABSTRACT

An anti-cancer composition comprising an effective amount of a *Rhus verniciflua* extract and a pharmaceutically acceptable carrier, the *Rhus verniciflua* extract being prepared by a process comprising extracting from *Rhus verniciflua* a crude extract with acetone or ethanol, and subjecting the crude extract to silica gel adsorption chromatography employing a mixture of chloroform and methanol.

3 Claims, 11 Drawing Sheets

PROCESS FOR THE PREPARATION OF *RHUS VERNICIFLUA* EXTRACT AND ANTI-CANCER COMPOSITION CONTAINING SAME

FIELD OF THE INVENTION

The present invention relates to a process for preparing an extract of *Rhus verniciflua* and an anti-cancer composition comprising the extract.

BACKGROUND OF THE INVENTION

Pharmaceutically useful compounds may be obtained from *Rhus verniciflua* which has been traditionally used in Korea, Japan and China in making a lacquer paint. For example, fisetin, fustin and other compounds have been found in the aqueous extract of the xylem of *Rhus verniciflua* (Hasegawa, M. and T. Shirato, *J. Chem. Soc.*, 72, 223 (1951)). Fisetin and fustin have pharmacological activity in: protecting blood vessel and capillary(Beretz, A. and Cazenave, J. P., "The Effect of Flavonoids on Blood Vessel Wall Interactions" in *Plant Flavonoids in Biology and Medicine: Biochemical, Pharmacological and Structure-Activity Relationships*, E. Middleton Jr. and J. B. Harborne, Eds., A. R. Liss, New York, pp 187–200 (1988)); suppressing the formation of peroxidized lipids(Kappus, H. et al., *Pharmacol.*, 300, 179–187(1977); Baumann, J. et al., *Prostaglandins*, 20, 627–639(1980); and Yoshimoto, T. et al., *Biochem. Biophys. Res. Commun.*, 116, 612–618 (1983)); and inhibiting allergy and dermatopathies(Loggia, R. D. et al., in Cody, V. et al.(eds), *Plant Flavonoids in Biology and Medicine*, A. R. Liss, New York, 481–484 (1986)).

Besides fisetin and fustin, various other flavonoids such as agathisflavone, butein, corilagin, 3',4'-dihydroxy flavone, eicosanedioic acid, europetin, sulfuretin and quercetin have also been found in the plants of genus Rhus(Bukkingham, *J. Dictionary of Natural Products*, 7, 761(1994)). However, none of these compounds has been tested for their anti-cancer activity.

As well known, cancer is a disease caused by the impediment of cell differentiation and loss of control over cell growth. Recently, agents that induce cancerous cells to differentiate into normal cells, i.e., organ differentiation agents, have been studied to treat various forms of cancer(V. L. Stevens, et al., *Cancer Res.*, 50, 222–226(1990)). In these studies, potential organ differentiation agents have been screened by employing an F9 teratocarcinoma cell model system. An F9 teratocarcinoma cell does not differentiate under a normal condition, but it transforms into a primitive developmental form when it reacts with retinoic acid, a synthetic organ differentiation agent. Further, this cell differentiates into a form similar to a coelomic wall when it reacts with a mixture of retinoic acid and dibutyryl cyclic AMP(Bt2cAMP) (Grober and Adamsom, Strickland and Sawey, 1980, 1986).

Such screening studies have shown that urusolic acid (UA), oleanolic acid(OA) and triterpene acid isolated from *Eriobotrva laponica* LINDL. are capable of differentiating F9 teratocarcinoma cells into normal cells. Further, urusolic acid and oleanolic acid have also been reported to have anti-cancer activity and to induce the differentiation of F9 teratocarcinoma cells by regulating the gene involved in the differentiation(Lee, H. Y. et al., *J. Cancer Res. Clin. Oncol.*, 120, 513–518(1994)).

Angiogenesis, on the other hand, is a process of forming new blood vessels, which occurs in the embryogenesis and at the recovery region of a wound and corpus luteum. It has been reported that angiogenesis is indispensable for cancer cells to grow and propagate to various parts of the body by metastasis(Folkman, J. and Klagsburn, M., *Science*, 235, 442–447 (1987); Liotta, L. A., et al., *Cancer Res.*, 34, 997–1004 (1974)). Accordingly, an agent that inhibits angiogenesis may be useful in blocking the metastasis of cancer cells after a surgical operation.

Retinoic acid and vitamin D3, which induce the differentiation of cancer cells to normal cells, inhibit angiogenesis as well(Okinawa, T. et al., *J. Antibiot.*, 44, 1033–1035 (1991)). However, there exist many problems in the clinical use of these angiogenesis inhibitors, due to their limited effect and high toxicity(Meeks, R. G. et al., *Arch. Biochem. Biophys.*, 207, 141–147(1981)). Accordingly, various efforts have been made to identify and isolate non-toxic natural angiogenesis inhibitors from plants. In this vein, urusolic acid and oleanolic acid isolated from *Eriobotrva japonica* LINDL. have been reported to have some inhibitory activity on angiogenesis(Sohn, K. H. and H. Y. Lee, *Cancer Letters*, 94, 213–128(1995)).

However, there has continued to exist a need to develop a non-toxic anti-cancer agent which has an improved therapeutic efficacy.

SUMMARY OF THE INVENTION

Accordingly, it is an object of the present invention to provide a process for preparing an extract of *Rhus verniciflua* which may be used as an effective anti-cancer agent of low toxicity.

Another object of the present invention is to provide an anti-cancer composition comprising an extract of *Rhus verniciflua*.

An additional object of the present invention is to provide an anti-oxidative composition comprising an extract of *Rhus verniciflua*.

A further object of the present invention is to provide a hangover resolving composition comprising an extract of *Rhus verniciflua*.

A still further object of the present invention is to provide a method for treating a patient suffering from a cancer by employing an extract of *Rhus verniciflua*.

In accordance with the present invention, there is provided a process for preparing an extract of *Rhus verniciflua*, which comprises extracting from *Rhus verniciflua* with acetone or ethanol a crude extract and subjecting the crude extract to silica gel adsorption chromatography employing a mixture of chloroform and methanol as an eluent to obtain the extract; and an anti-cancer composition comprising the extract of *Rhus verniciflua* prepared by the inventive process as an active ingredient in combination with a pharmaceutically acceptable carrier.

BRIEF DESCRIPTION OF THE DRAWINGS

The above and other objects and features of the present invention will become apparent from the following description of the invention, when taken in conjunction with the accompanying drawings, in which:

FIGS. 7A and 7B illustrate the organ differentiation inductive activity of the extract of *Rhus verniciflua*, wherein FIG. 7A shows F9 teratocarcinoma cells and FIG. 7B, the organ differentiation-induced normal cells;

DETAILED DESCRIPTION OF THE INVENTION

The extract of *Rhus verniciflua* of the present invention is prepared as follows. The woody part of *Rhus verniciflua* is cut and dried in the shade for 1 week to 3 months, preferably, 1 month. The dried woody part may be crushed, if necessary. The woody part of the *Rhus verniciflua* may be processed into the form of wood chips or sawdust without the drying process.

To 100 g of the processed woody part of the *Rhus verniciflua*, an organic solvent is added in an amount ranging from 0.3 to 1 l, and the mixture is allowed to stand at a temperature ranging from 20 to 60° C., preferably, 40° C., for a period ranging from 1 to 30 days, preferably, 5 days, to obtain a yellow crude extract. Exemplary organic solvent useful in the present invention includes acetone, ethanol, methanol and a mixture thereof. Acetone is preferably an acetone-based solvent having an acetone content of 90% or more, preferably 99%, and ethanol is preferably an ethanol-based solvent having an ethanol content of 80% or more, preferably, 80%.

Then, water is added to the crude extract, and the mixture is partitioned to obtain a water-soluble fraction. The water-soluble fraction is filtered and then concentrated.

The resulting concentrate is dried and subjected to silica gel adsorption column chromatography using as an eluent a mixture of chloroform and methanol, preferably mixed in a ratio ranging from 9:1 to 7:3(v/v), until yellow extract is completely eluted. The combined extract is concentrated under a reduced pressure and then dried to obtain the inventive *Rhus verniciflua* extract.

Figure 1:
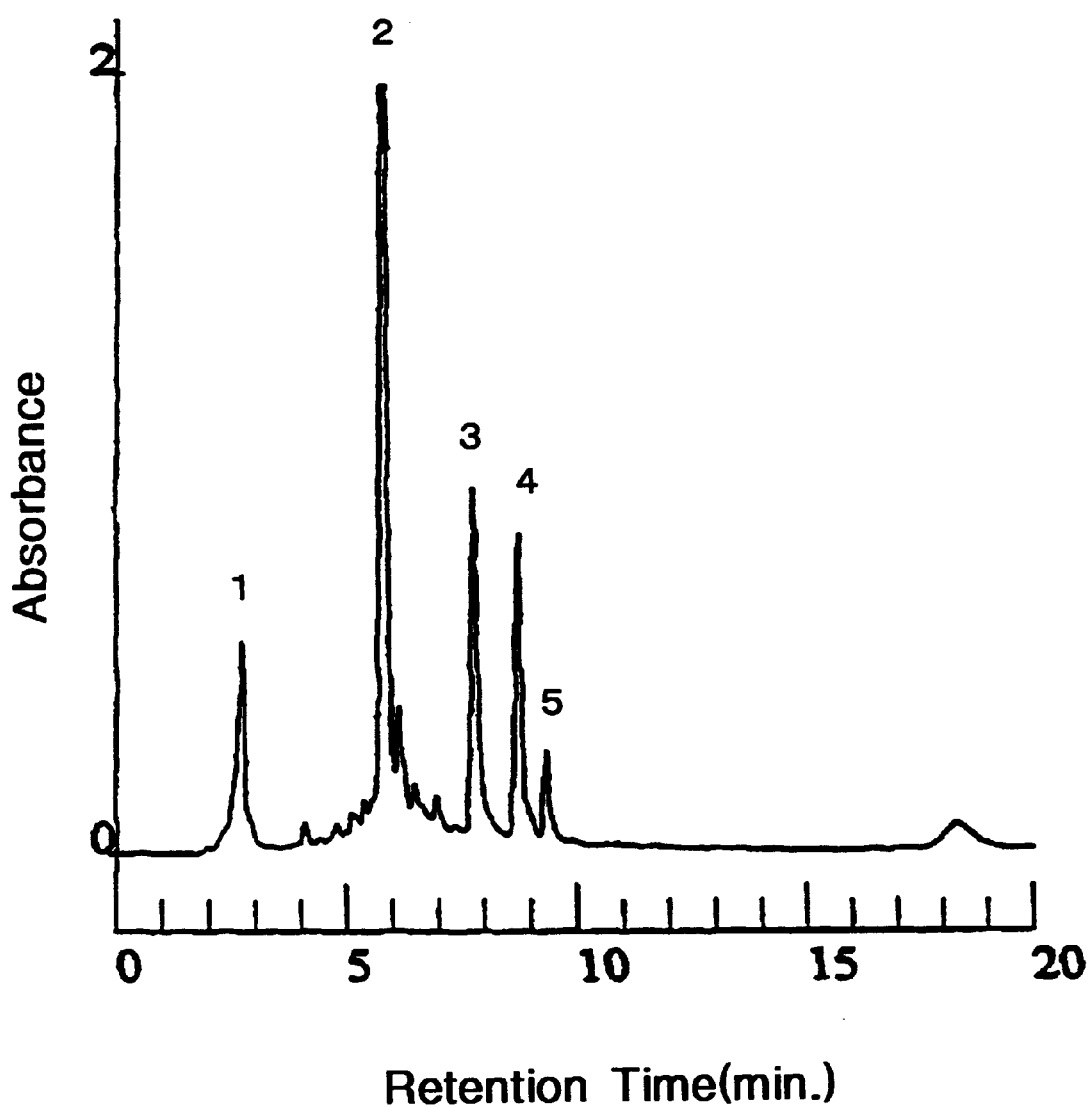
FIG. 1 shows the high pressure liquid chromatography (HPLC) scan of the extract of *Rhus verniciflua*.

Analysis by high pressure liquid chromatography(HPLC) revealed that the inventive extract is a mixture consisting of five components. FIG. 1 shows the HPLC scan of the extract of *Rhus verniciflua*, wherein Peak 1 is a novel compound having a molecular weight of 162; Peak 2, fustin(3,3',4',7-tetrahydroxyflavanone) having a molecular formula of $C_{15}H_{12}O_6$(Mw: 288); Peak 3, fisetin(3,3',4',7-tetrahydroxyflavone) having a molecular formula of $C_{15}H_{10}O_6$(Mw: 286); Peak 4, sulfuretin(3',4',6'-trihydroxyaurone) having a molecular formula of $C_{15}H_{10}O_5$ (Mw: 272); and Peak 5, butein(2',3,4,4'-tetrahydroxychalcone) having a molecular formula of $C_{15}H_{12}O_5$ (Mw: 272).

The inventive extract of *Rhus verniciflua* obtained as above exhibits anti-cancer, organ differentiation inductive and angiogenesis inhibitory activities, as well as anti-oxidative and hangover resolving activities. Accordingly, the inventive extract may be employed as a preventive or treating agent for the occurrence and metastasis of a cancer. Further, it may also be used as an anti-oxidative or hangover resolving agent.

Accordingly, the present invention also provides a pharmaceutical composition for use as an anti-cancer agent, an anti-oxidative agent or a hangover resolving agent, which comprises the extract of *Rhus verniciflua* as an active ingredient, in combination with pharmaceutically acceptable excipients, carriers or diluents.

A pharmaceutical formulation may be prepared by using the composition in accordance with any of the conventional procedures. In preparing the formulation, the active ingredient is preferably admixed or diluted with a carrier, or enclosed within a carrier which may be in the form of a capsule, sachet or other container. When the carrier serves as a diluent, it may be a solid, semi-solid or liquid material acting as a vehicle, excipient or medium for the active ingredient. Thus, the formulations may be in the form of a tablet, pill, powder, sachet, elixir, suspension, emulsion, solution, syrup, aerosol, soft and hard gelatin capsule, sterile injectable solution, sterile packaged powder and the like.

Examples of suitable carriers, excipients, and diluents are lactose, dextrose, sucrose, sorbitol, mannitol, starches, gum acacia, alginates, gelatin, calcium phosphate, calcium silicate, cellulose, methyl cellulose, microcrystalline cellulose, polyvinylpyrrolidone, water, methylhydroxybenzoates, propylhydroxybenzoates, talc, magnesium stearate and mineral oil. The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a mammal by employing any of the procedures well known in the art.

The pharmaceutical formulation of the present invention can be administered via various routes including oral, transdermal, subcutaneous, intravenous and intramuscular introduction. For treating a human patient, a typical daily dose of the extract of *Rhus verniciflua* may range from about 10 to 100 mg/kg body weight, preferably 15 to 60 mg/kg body weight, and can be administered in a single dose or in divided doses. However, it should be understood that the amount of the active ingredient actually administered ought to be determined in light of various relevant factors including the condition to be treated, the chosen route of administration, the age, sex and body weight of the individual patient, and the severity of the patient's symptom; and, therefore, the above dose should not be intended to limit the scope of the invention in any way.

Accordingly, the present invention also provides a method for treating a patient suffering from a cancer, which comprises administering an effective amount of the extract of *Rhus verniciflua* to the patient.

The following Examples are intended to further illustrate the present invention without limiting its scope.

Further, percentages given below for solid in solid mixture, liquid in liquid, and solid in liquid are on a wt/wt, vol/vol and wt/vol basis, respectively, unless specifically indicated otherwise.

EXAMPLE 1

Preparation of Extract of *Rhus verniciflua*

(Step 1) Preparation of crude extract

*Rhus verniciflua* was cut into a length of 10 cm and dried in the shade for 1 month. 4 l of 99.9% acetone was added to 400 g of the dried *Rhus verniciflua* and the mixture was allowed to stand at 40° C. for 5 days to obtain a yellow extract. To the extract was added an equal volume of water and the mixture was stirred at 40° C. and then cooled to room temperature. The resulting mixture was filtered through No. 2 filter(Watman, U.S.A.) and the filtrate was concentrated at a reduced pressure by using a rotary vacuum evaporator(Labo rota 300, Resona Co., Swiss). The concentrate was dried with a centrifugal vacuum drier(Centrabag vision, Korea) to obtain 4.4 g of a crude extract(yield: 1.1%).

(Step 2) Silica gel adsorption chromatography

The crude extract obtained in Step 1 was purified by silica gel adsorption chromatography as follows. 40 g of silica gel (230–400 mesh, for chromatographic use, Merck) which had previously been activated at 130° C. for 3 hours was slurried with n-hexane, and then packed in a glass open column(2.9× 45 cm). For the purpose of removing moisture in the crude extract, 7 g of calcium sulfate was filled in the top portion of column. 4 g of the crude extract was dissolved in 6 ml of methanol, loaded on the column, and then using a chloroform:methanol mixture(90:10(v/v)) the yellow extract was eluted completely. Yellow eluates were combined and concentrated under a reduced pressure with a rotary vacuum evaporator(Labo rota 300, Resona Co., Swiss), and dried at 40° C. with a centrifugal vacuum drier(Centrabag vision, Korea) to obtain 3 g of a crude extract(yield: 75%).

EXAMPLE 2

Analysis of Extract of *Rhus verniciflua*

(Step 1) Resolution of components by high pressure liquid chromatography

The extract of *Rhus verniciflua* obtained in Example 1 was mixed with an equal volume of methanol. The mixture was pre-treated with $C_{18}$-type Sep-pak(Waters, U.S.A.) and then filtered through a 0.2 μm syringe filter(Satorius, Germany). The filtrate was injected to DX-300 Bio HPLC (Dionex) equipped with an RCM 8×10 column (Waters, U.S.A.) and a $C_{18}$ 8×10 cartridge column(Nova-Pak) and then eluted by using a mixture of water and methanol under the condition listed in Table 1. The chromatography was conducted using a sample size of 50 μl, and the eluate was detected at 254 nm with a DX-300 UV detector.

TABLE 1

| Time (min) | Flow rate (ml/min) | Eluent Water (%) | Methanol (%) | Curve |
|---|---|---|---|---|
| 0.0 | 1.5 | 80 | 20 | 5 |
| 0.5 | 1.5 | 80 | 20 | 5 |
| 3.0 | 1.5 | 50 | 50 | 5 |
| 12.8 | 1.5 | 20 | 80 | 5 |

TABLE 1-continued

| Time (min) | Flow rate (ml/min) | Eluent Water (%) | Methanol (%) | Curve |
|---|---|---|---|---|
| 14.9 | 1.5 | 0 | 100 | 5 |
| 16.7 | 1.5 | 0 | 100 | 5 |
| 18.6 | 1.5 | 80 | 20 | 5 |
| 20.0 | 1.5 | 80 | 20 | 5 |

The resulting HPLC chromatogram shown in FIG. 1 reveals that the extract of *Rhus verniciflua* is a mixture of five components. The content of each component is shown in Table 2.

TABLE 2

| Component | Peak 1 | Peak 2 | Peak 3 | Peak 4 | Peak 5 |
|---|---|---|---|---|---|
| Content (%) | 10.00 | 40.69 | 10.80 | 9.56 | 2.43 |

(Step 2) Analysis of respective component

Each component obtained in Step 1 was analyzed by the combined use of a mass spectrometer(JEOL JMS-AX 505 WA, Japan; Injection: direct injection, Ion mode: EI+, Temp.: 71.4° C., Output m/z range: 50–302) and an element analyzer(Perkin-Elmer, U.S.A.). The results exhibited that Peak 1 is a novel compound having a molecular weight of 162; Peak 2, fustin(3,3',4',7-tetrahydroxyflavanone) having a molecular formula of $C_{15}H_{12}O_6$(Mw: 288)(white crystals); Peak 3, fisetin(3,3',4',7-tetrahydroxyflavone) having a molecular formula of $C_{15}H_{10}O_6$(Mw: 286)(yellow crystals); Peak 4, sulfuretin(3',4',6'-trihydroxyaurone) having a molecular formula of $C_{15}H_{10}O_5$(Mw: 272)(deep orange crystals); and Peak 5, butein(2',3,4,4'-tetrahydroxychalcone) having a molecular formula of $C_{15}H_{12}O_5$ (Mw: 272)(orange crystals).

EXAMPLE 3

Anti-Cancer Activity of Extract of *Rhus verniciflua*

In accordance with MTT(3-(4,5-dimethylthiazol-2-yl)-2, 5-diphenyltetrazolium bromide) test method(J. Carmicheal, et al., *Cancer Res.*, 47, 936(1987)), each of tumor cell lines L1210(mouse blood cancer cell, Deposit No.: ATCC CCL219), A549(human lung cancer cell, Deposit No.: ATCC CCL185), SKOV-3 (human uterine cancer cell, Deposit No.: ATCC HTB77), SKMEL-2(human skin cancer cell, Deposit No.: ATCC HTB68), HCT-15(human colon cancer cell, Deposit No.: ATCC CCL225) and XF-498 (human central nervous system cancer cell, obtained from NCI) was suspended in 0.2% trypan blue to prepare a unicellular suspension. The suspension was placed in a hemacytometer(Superior, Germany) and the number of living cells was counted under an inverted microscope.

A mixed medium consisting of 90% RPMI-1640 medium (Gibco) and 10% fetal bovine serum was added to each well of a 96-well cell culture plate(Becton Dickinson Labware, U.S.A.) in an amount of 135 μl/well and each of the cell line suspensions prepared above was added thereto in an amount of $3 \times 10^3$ cells/well. The crude extract of *Rhus verniciflua* prepared in Step 1 of Example 1 and the extract of *Rhus verniciflua* prepared in Step 2 of Example 1 were serially diluted with phosphate buffered saline(PBS) in the ranges from 30 μg/ml to 0.3 μg/ml and from 100 μg/ml to 1 μg/ml, respectively, and these solutions were added to test group wells in an amount of 15 μl/well. PBS was added to control group wells.

The cell culture plate was incubated at 37° C. under 5% $CO_2$ for 3 days for L1210 cell line, and for 4 days for other cell lines. Then, 2 mg/ml MTT solution was added to the wells in an amount of 50 μl/well and the plate was incubated at 37° C. under 5% $CO_2$ for another 4 hours. The supernatant of the culture was removed by using multiple channel pipette(Biohit OY, Finland), dimethyl sulfoxide(DMSO) was added to the wells in an amount of 150 μl/well and the plate was shaken for 15 min. Accordingly, the optical density(O.D.) of each well was determined at 540 nm with an ELISA reader(Dynatech, MR5000).

50% inhibition concentration($IC_{50}$) stands for the concentration of the test compound in the test group well showing an O.D. corresponding to 50% of that of the control group well. The experiment was repeated three times, the cytotoxicity of the test group at each concentration was calculated by the following equation and the $IC_{50}$ was determined using the linear regression method:

$$\text{Cytotoxicity} \atop (\%) = \left[ 1 - \frac{\text{Mean } OD \text{ of the test group well} - \text{Mean } OD \text{ of the Background well}}{\text{Mean } OD \text{ of the cont. group well} - \text{Mean } OD \text{ of the Background well}} \right] \times 100$$

The background well means a well containing PBS only.

A natural product is considered to have a good anti-cancer activity when its $IC_{50}$ is lower than 30 μg/ml. In view of this, the crude extract of *Rhus verniciflua* prepared in Step 1 of Example 1 has good anti-cancer activities against most of the cell lines as shown in Table 3.

TABLE 3

| $IC_{50}$ (μg/ml) | | | | | |
|---|---|---|---|---|---|
| L1210 | A549 | SK-OV-3 | SKMEL-2 | HCT15 | XF-498 |
| 10.5 | 47.8 | 26.9 | 12.8 | 14.6 | 17.75 |

Further, as shown in Table 4, the extract of *Rhus verniciflua* prepared in Step 2 of Example 1 exhibits $IC_{50}$ lower than that of the crude extract in most of the cell lines. This result suggests that impurities removed during the purification process do not have anti-cancer activity.

TABLE 4

| $IC_{50}$ (μg/ml) | | | | | |
|---|---|---|---|---|---|
| L1210 | A549 | SK-OV-3 | SKMEL-2 | HCT15 | XF-498 |
| 14.7 | 18.24 | 17.67 | 20.03 | 14.38 | 17.50 |

Figure 2:
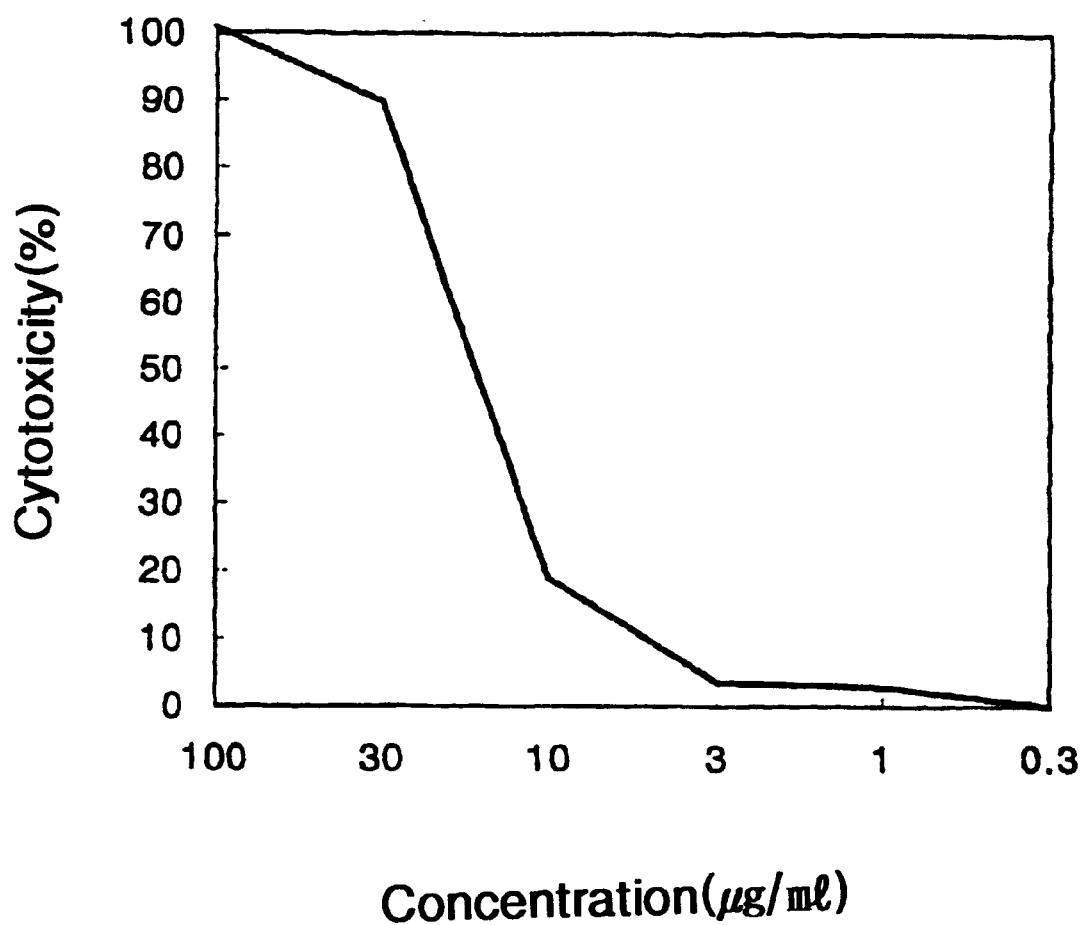
FIG. 2 depicts the activity of the extract of *Rhus verniciflua* against human lung cancer cells(A549)
Figure 3:
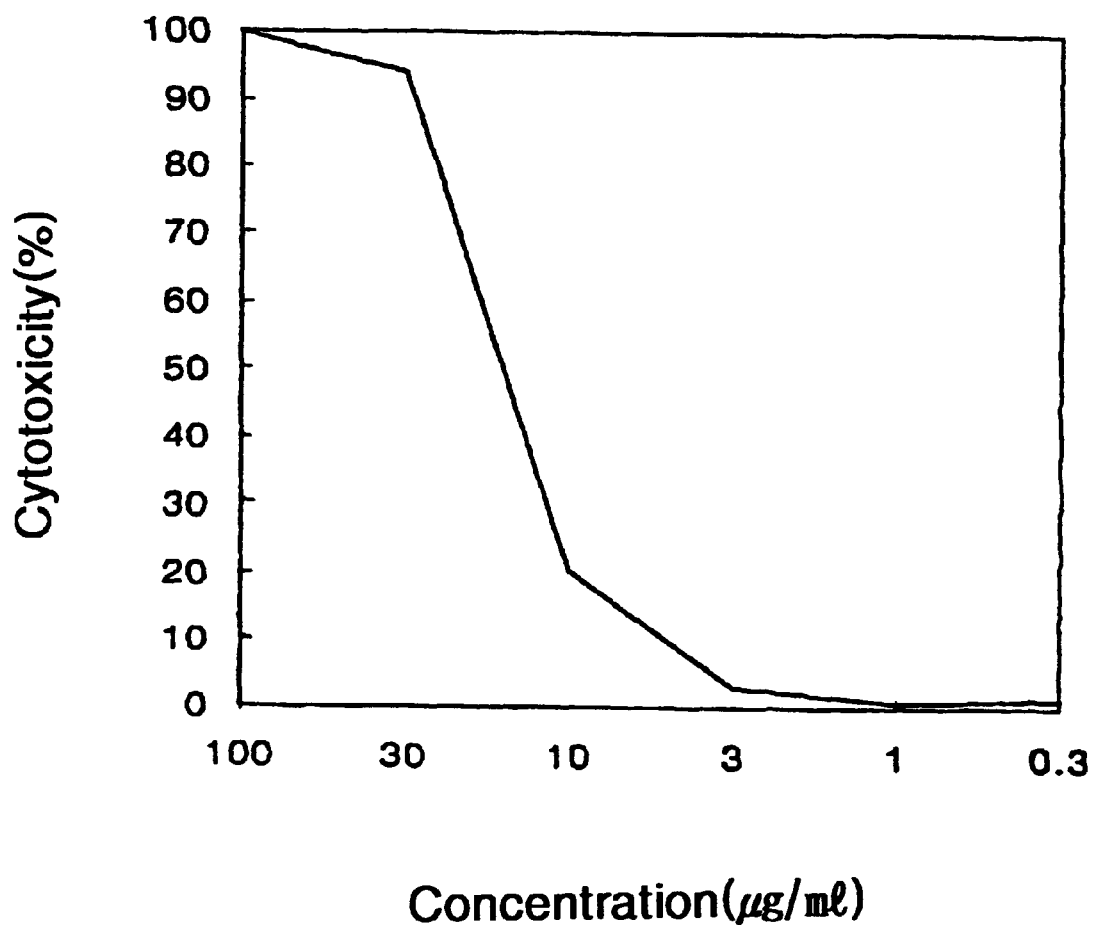
FIG. 3 represents the activity of the extract of *Rhus verniciflua* against human uterine cancer cells(SKOV-3)
Figure 4:
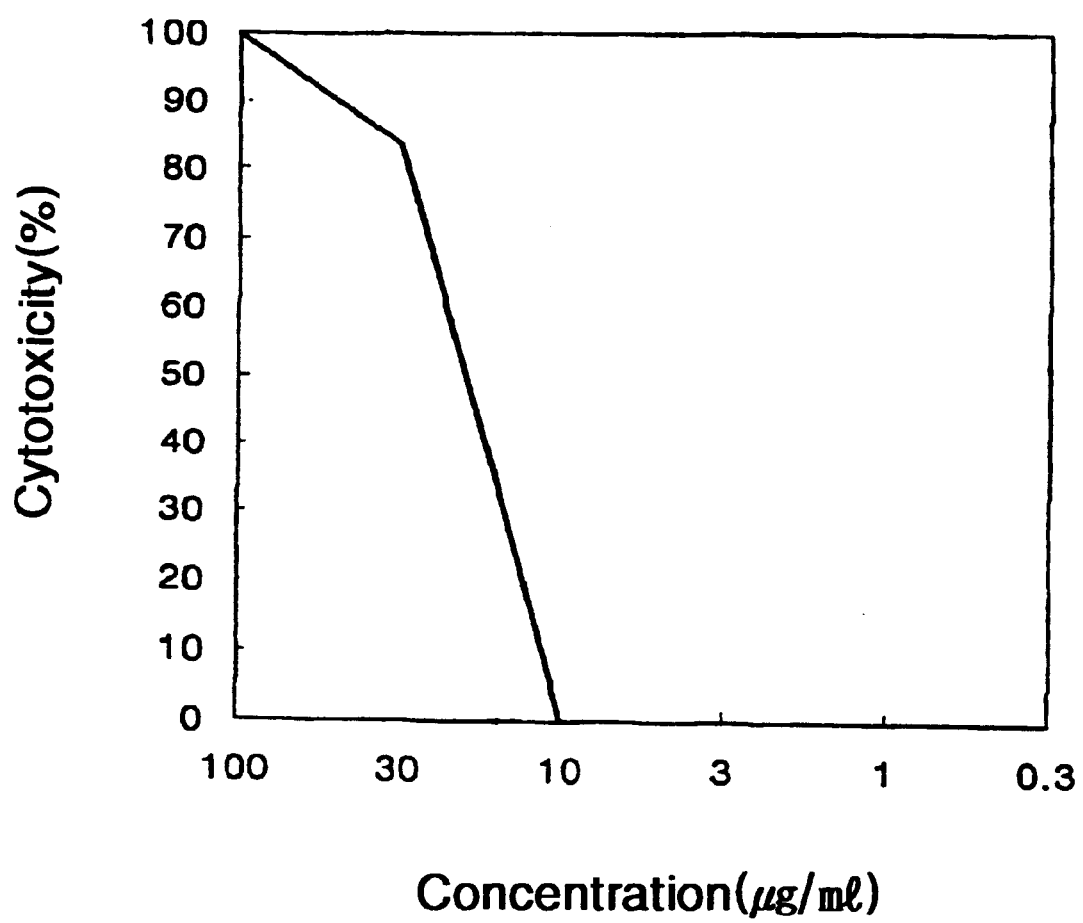
FIG. 4 discloses the activity of the extract of *Rhus verniciflua* against human skin cancer cells(SKMEL-2)
Figure 5:
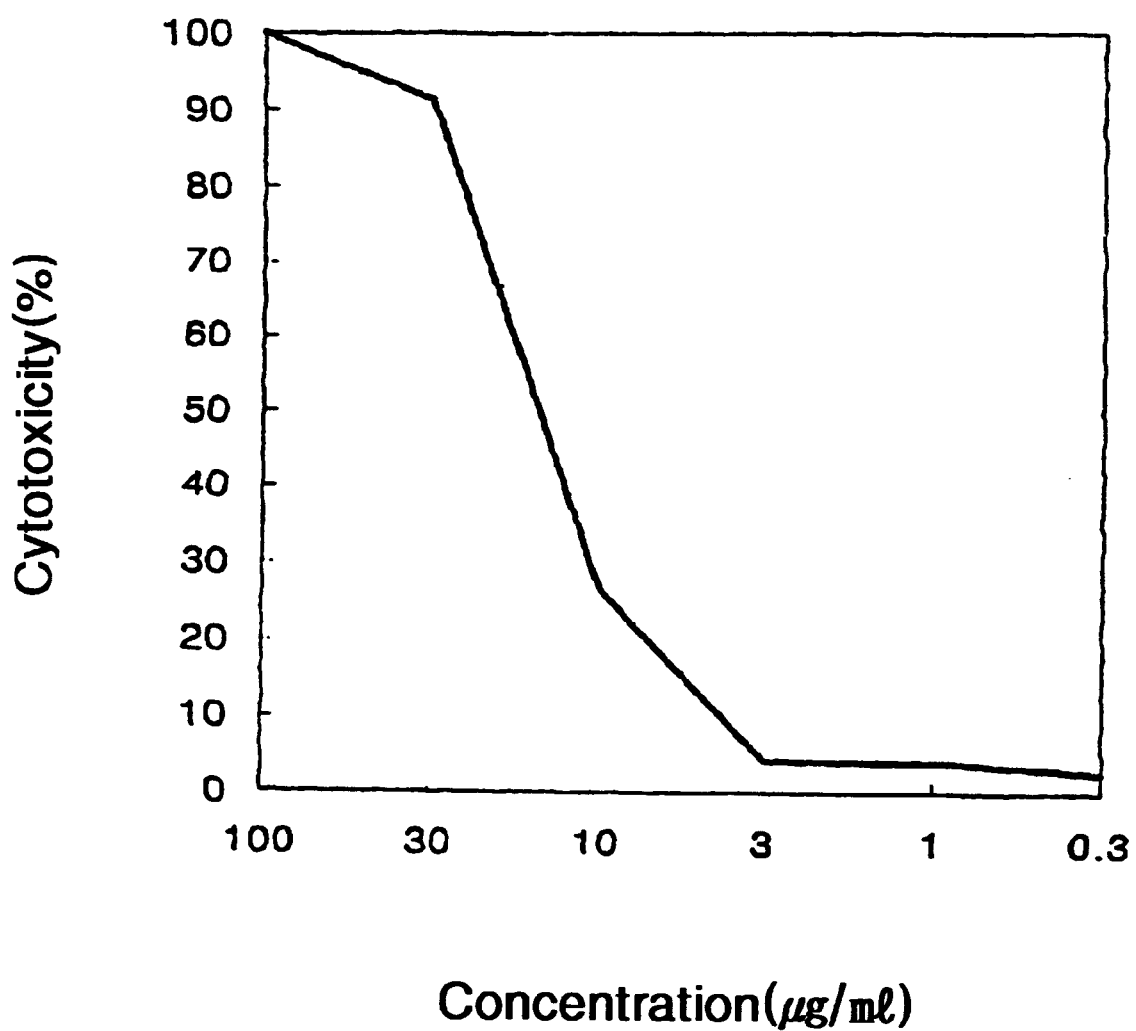
FIG. 5 presents the activity of the extract of *Rhus verniciflua* against human central nervous system cancer cells (XF-498)
Figure 6:
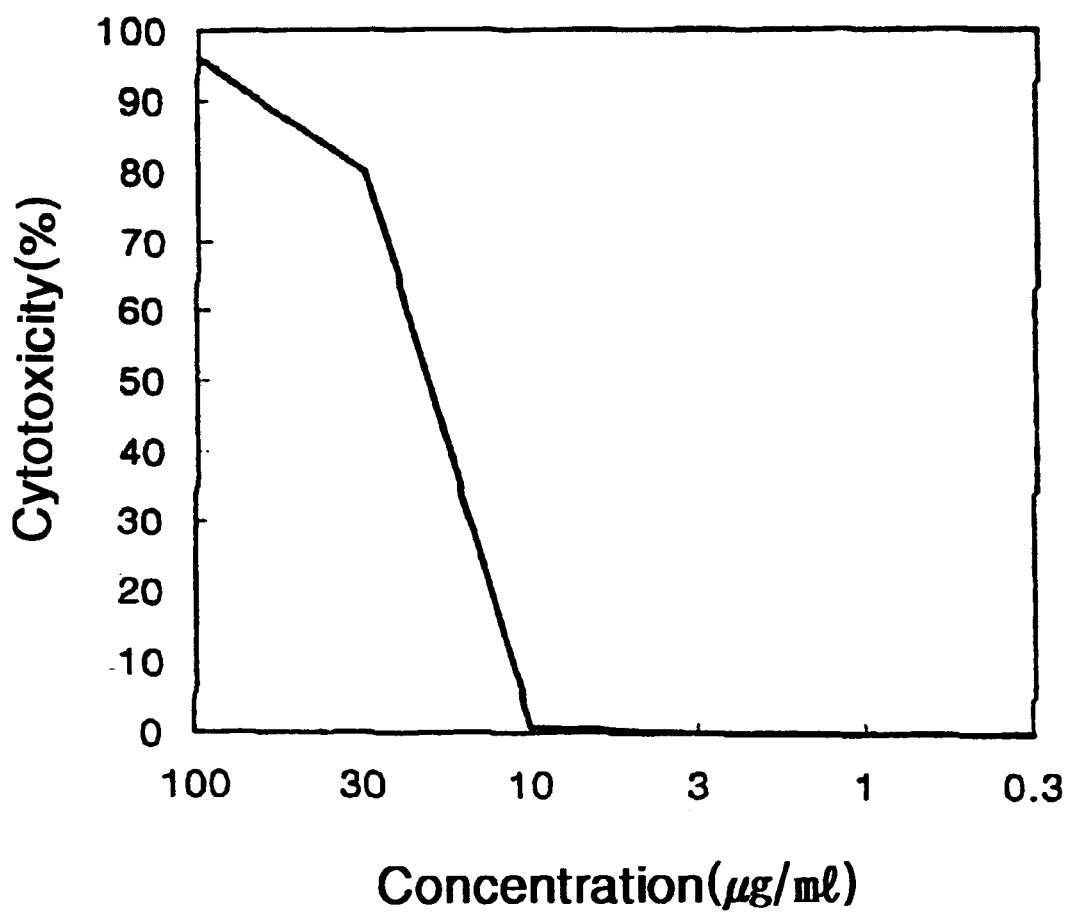
FIG. 6 exhibits the activity of the extract of *Rhus verniciflua* against human colon cancer cells(HCT-15)

FIGS. 2 to 6 show the anti-cancer activity of the extract of *Rhus verniciflua* on various cancer cell lines relative to its concentration. Specifically, FIG. 2 shows the anti-cancer activity against human lung cancer cell (A549); FIG. 3, against human uterine cancer cell (SKOV-3); FIG. 4, human skin cancer cell(SKMEL-2); FIG. 5, human central nervous system cancer cell(XF-498); and FIG. 6, human colon cancer cell(HCT-15).

EXAMPLE 4

Effect of Extract of *Rhus verniciflua* on Differentiation of Cancer Cell to Normal Cell F9 cells(mouse teratocarcinoma cell, Deposit No.: ATCC CRL 1720) were cultured on Dulbecco's modified Eagle's medium(DMEM, Gibco) containing 10% fetal calf serum (FCS) and 100 μg/ml of penicillin(Gibco) at 37° C. under 5% $CO_2$.

A unicellular suspension of subcultured F9 teratocarcinoma cells was added to a 75 $cm^2$ culture flask containing 2.5% FCS so that the ratio of the medium and the unicellular suspension became 90:10, and cultured at 37° C. under 5% $CO_2$ for 24 hours. For testing differentiation inductive activity, a composition("MU2CT") consisting of 50 μg of the extract of *Rhus verniciflua* obtained in Example 1("MU2"), 0.5 mM of Bt2cAMP and 0.25 mM of theophylline was added to the culture of F9 teratocarcinoma cells.

On the other hand, in order to confirm whether the conversion of a cancer gene by retinoic acid, which is currently used as a differentiation inducer, expresses LamBl, i.e., a differentiation-specific gene of mRNA, a composition ("RACT") consisting of 1 μg of retinoic acid, 0.5 mM of Bt2cAMP and 0.25 mM of theophylline was added to the culture of F9 teratocarcinoma cells.

The above cultures were cultured for 7 days, while adding the above-mentioned amounts of MU2CT and RACT to the respective cultures every 2 days. The cultures were then centrifuged at 1,500 rpm for 15 min., the supernatants were discarded and the cell pellets attached to the bottom of the tubes were suspended with fresh medium to obtain unicellular suspensions. The suspensions were observed under a phase contrast microscope to confirm whether the F9 teratocarcinoma cells were converted to round cells.

Further, in order to confirm whether the differentiation inductive activity was caused by a change in the cancer gene, a northern blotting analysis was carried out(Lee, H. Y. and H. Y. Chung, *J. Cancer Res. Clin. Oncol.*, 120, 513–518 (1994)).

Figure 7A:
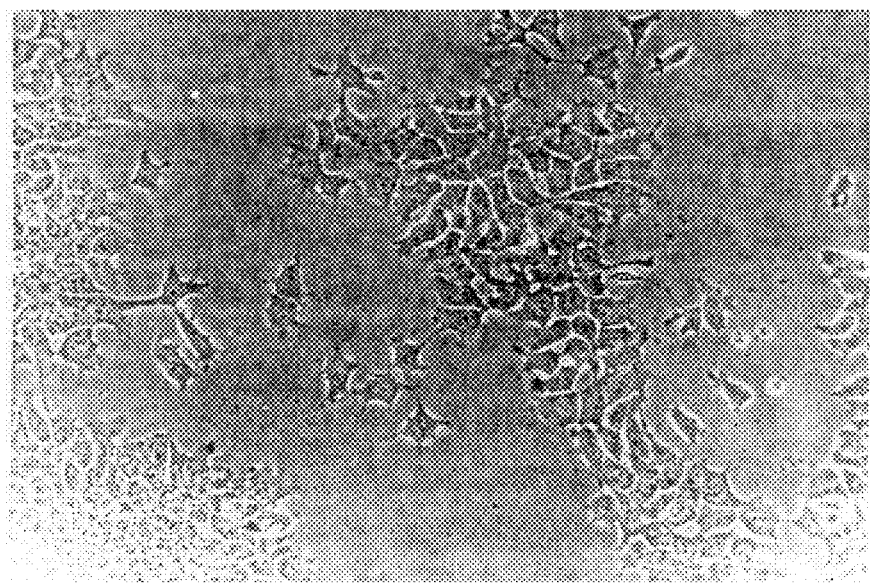
Figure 7B:
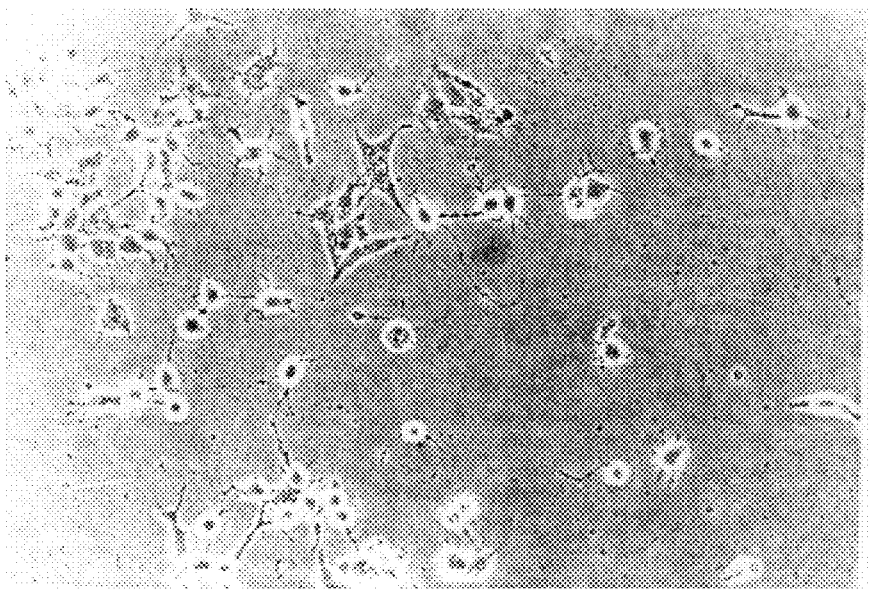

FIGS. 7A and 7B illustrate the organ differentiation inductive activity of the extract of *Rhus verniciflua*: FIG. 7A shows the F9 teratocarcinoma cells and FIG. 7B, the normal cells induced by organ differentiation. As can be seen from FIGS. 7A and 7B, the treatment of F9 teratocarcinoma cell with the extract of *Rhus verniciflua* induced the differentiation of angular cancer cells(7A) to round normal organ cells(7B).

Figure 8:
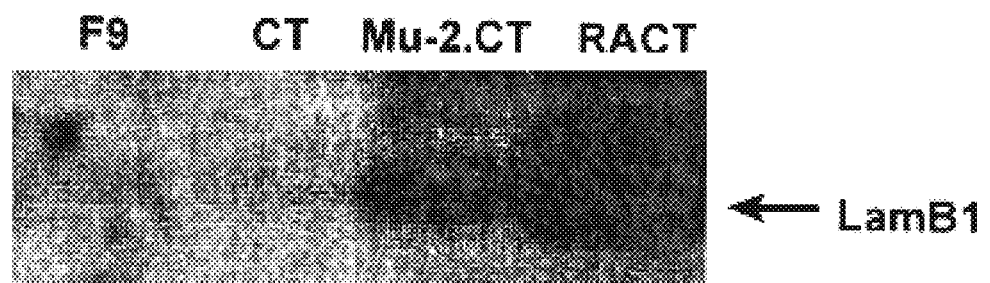
FIG. 8 provides the result of northern blotting analysis to measure the organ differentiation inductive activity of the extract of *Rhus verniciflua*.
Figure 8:
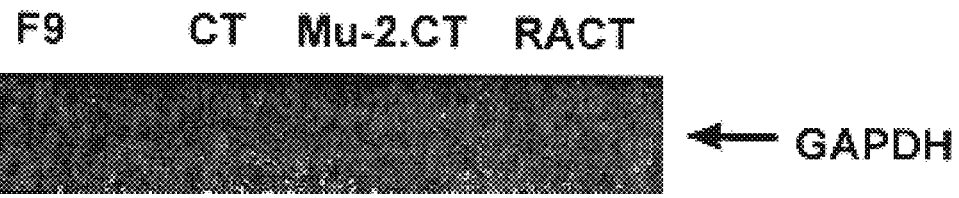

FIG. 8 shows the result of northern blotting analysis confirming the organ differentiation inductive effect of the extract of *Rhus verniciflua*. As can be seen from this result, retinoic acid, which is currently used as an organ differentiation inducer, converts the gene of the cancer cell to express LamBl gene, i.e., a differentiation-specific gene of mRNA. The composition containing *Rhus verniciflua* extract (MU2CT) is also exhibited to express LamBl gene. The non-treated F9 cells(F9) and F9 cells treated with 0.5 mM Bt2cAMP and 0.25 mM teophiline(CT), which are used as catalysts for organ differentiation induction, do not express LamB1 gene. On the other hand, the GAPDH gene, a control which is not a differentiation-specific gene, was expressed in all of the treated groups. Accordingly, it was confirmed that the extract of *Rhus verniciflua* (MU2) induces the organ differentiation of cancer cells into normal cells by converting the gene of the cancer cell.

EXAMPLE 5

Angiogenesis Inhibitory Activity of Extract of *Rhus verniciflua*

Twenty fertilized chicken eggs were kept for 3 days in a humidified egg incubator at 37° C. A small aperture was made on the pointed end of each egg, and 2 me of albumin was removed therefrom with an 18-gauge hypodermic syringe. At day 4, the portion of the shell covering the air sac was removed with forceps and the surface membrane of the air sac was peeled off. Subsequently, a test for the angiogenesis inhibitory effect was conducted by using an embryo having chorioallantois of 4 mm thickness.

The extract of *Rhus verniciflua* obtained in Example 1 was diluted with triply distilled water to a concentration ranging from 10 μg/ml to 100 μg/ml. 5 μl each of the dilutions was dropped on a sterilized Thermanox 15 mm cover slip(Nunc Inc., U.S.A.) to be air-dried. When the cover slip became dry, it was put on the surface of the chorioallantois of the embryo so that the surface thereof containing the extract of *Rhus verniciflua* contacts with the surface of the chorioallantois. Then, the end region of the air sac wherein egg shell remains was sealed with a tape.

After 2 days, a suitable amount of 10% lipid emulsifier (Green Cross, Korea) was injected to the chorioallantois with a 33-gauge syringe to contrast red blood vessels of the chorioallantois against the white lipid. The angiogenesis inhibitory effect was confirmed by counting the blood vessels under the cover slip in accordance with the method of Crum, R. et al. (*Science*, 230, 1375–1378 (1985)). Inhibition of blood vessels branching at a branching site was marked as positive and the occurrence rate was calculated.

Figure 9A:
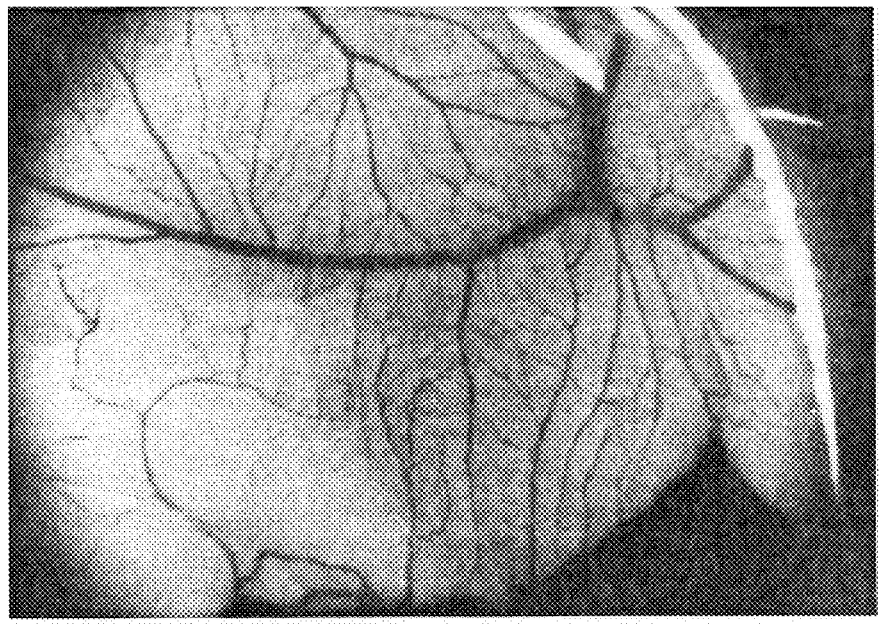
FIGS. 9A and 9B demonstrate the angiogenesis inhibitory activity of the extract of *Rhus verniciflua*, wherein 9A represents an egg of non-treated control group and, 9B, an egg treated with the extract of *Rhus verniciflua*.
Figure 9B:

FIGS. 9A and 9B show the angiogenesis inhibitory activity of the extract of *Rhus verniciflua:* 9A represents the control egg and 9B, the egg treated with the extract of *Rhus verniciflua*.

The angiogenesis inhibition rate of the extract of *Rhus verniciflua* is shown as a percentage of number of inhibited blood vessels/number of total blood vessels as shown in Table 5.

TABLE 5

| Group | | Angiogenesis inhibition rate (%) | # of inhibited blood vessels/ # of total blood vessels |
| --- | --- | --- | --- |
| Comparative group (non-treated group) | | 14 | 2/14 |
| Extract of R. verniciflua (μg/ml) | 10 | 31 | 4/13 |
| | 50 | 45 | 5/11 |
| | 100 | 79 | 11/14 |

EXAMPLE 6

Anti-oxidative Activity of Extract of *R. verniciflua*

DPPH(1,1-diphenyl-2-picrylhydrazyl) is a free radical which is very stable in an organic solution. It is a purple compound exhibiting characteristic light absorption at 517 nm and its purple color is decolorized by a proton radical scavenger. Accordingly, it is advantageously employed in measuring anti-oxidative activity of a material.

DPPH was dissolved in absolute ethanol to a concentration of 0.1 mmol/ml("DPPH ethanol solution"). To this solution, the extract of *R. verniciflua* obtained in Example 1 and Sesamol (Sigma, U.S.A.), a natural anti-oxidant were added to a concentration of 0.04%, respectively to obtain an "extract ethanol solution" and a "Sesamol ethanol solution".

2 ml of the DPPH ethanol solution was put into each of two 4 me disposable spectrophotometer cuvettes(Muller ratiolab, Germany). Then, 2 ml of the extract ethanol solution was placed in one cuvette and 2 ml of the Sesamol ethanol solution was put into the other cuvette. The mixtures were reacted at room temperature for 30 min. As a control, a cuvette containing 4 ml of the DPPH ethanol solution was used. The absorption of each cuvette was determined at 517 nm with a spectrophotometer(HP 8453 diode array spectrophotometer). The absorption of the extract ethanol solution was calibrated with the absorption of the control, and the capability of the extract ethanol solution to decolorize the purple color of the DPPH ethanol solution was calculated based on the calibrated absorption of the Sesamol ethanol solution.

Figure 10:
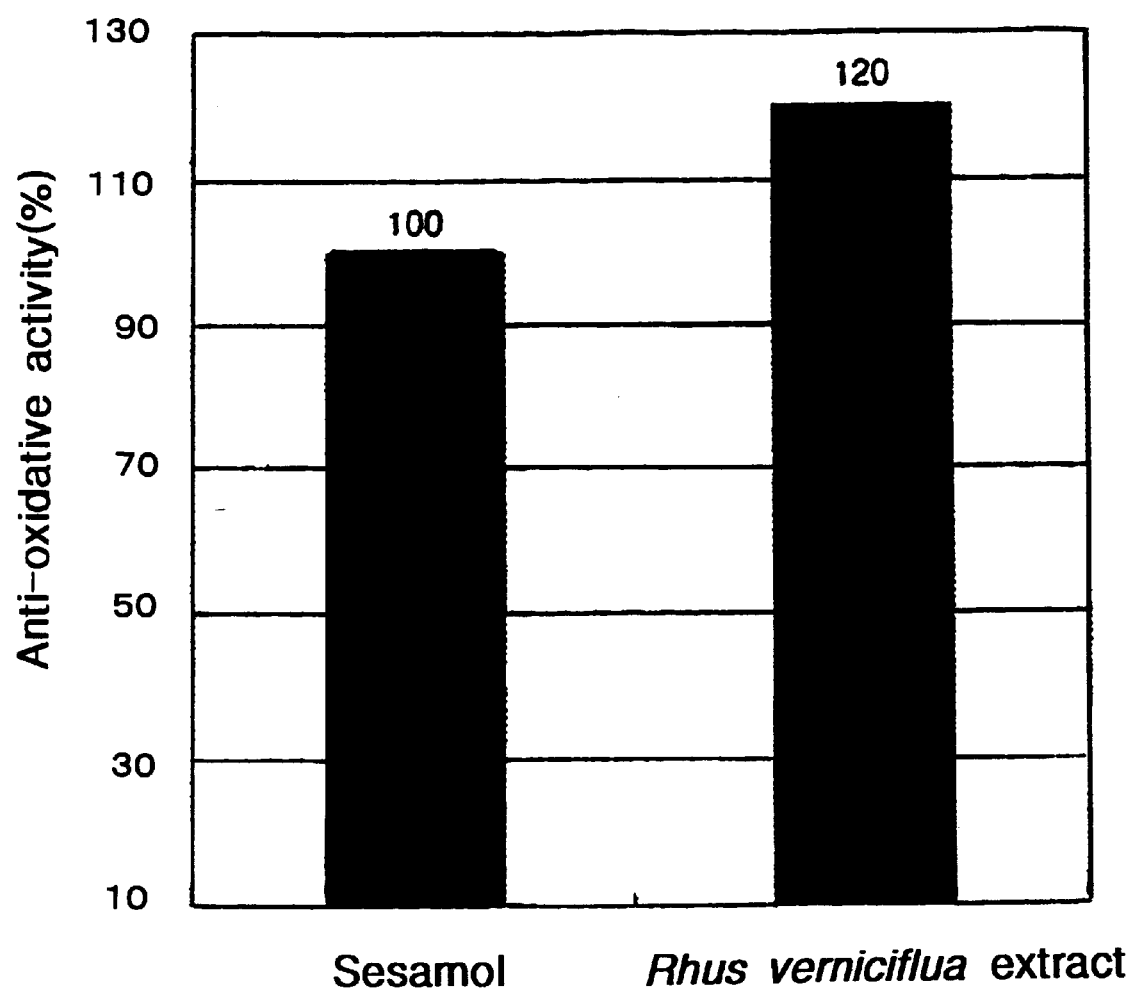
FIG. 10 compares the anti-oxidative activity of the extract of *Rhus verniciflua* with that of Sesamol.

FIG. 10 compares the anti-oxidative effect of the extract of *Rhus verniciflua* with that of Sesamol, wherein the extract of *Rhus verniciflua* exhibits an anti-oxidative activity of 120 relative to Sesamol's 100. That is, the extract of *Rhus verniciflua* exhibits a 20% high anti-oxidative activity than Sesamol.

EXAMPLE 7

Hangover Resolving Activity of Extract of *R. verniciflua*

Ten three-week old Sprague-Dawley rats were put on a 24-hour fast while allowing water. Thereafter, 2 ml of 40% ethanol was orally administered by force with 10 cm stainless steel sonde and the rats were divided into two groups. After 1 hour, the rats of one group were orally administered with 2 ml of water(control group) and the rats of the other group, with 2 ml of 500 mg/me aqueous solution of the extract of *Rhus verniciflua* (test group). After 4 hour, blood samples were taken from the hearts of the rats and the blood alcohol concentration was determined in accordance with the method of Bergmeyer (*Methods of Enzymatic Analysis*, 3rd Ed., 598–602(1984)).

Figure 11:
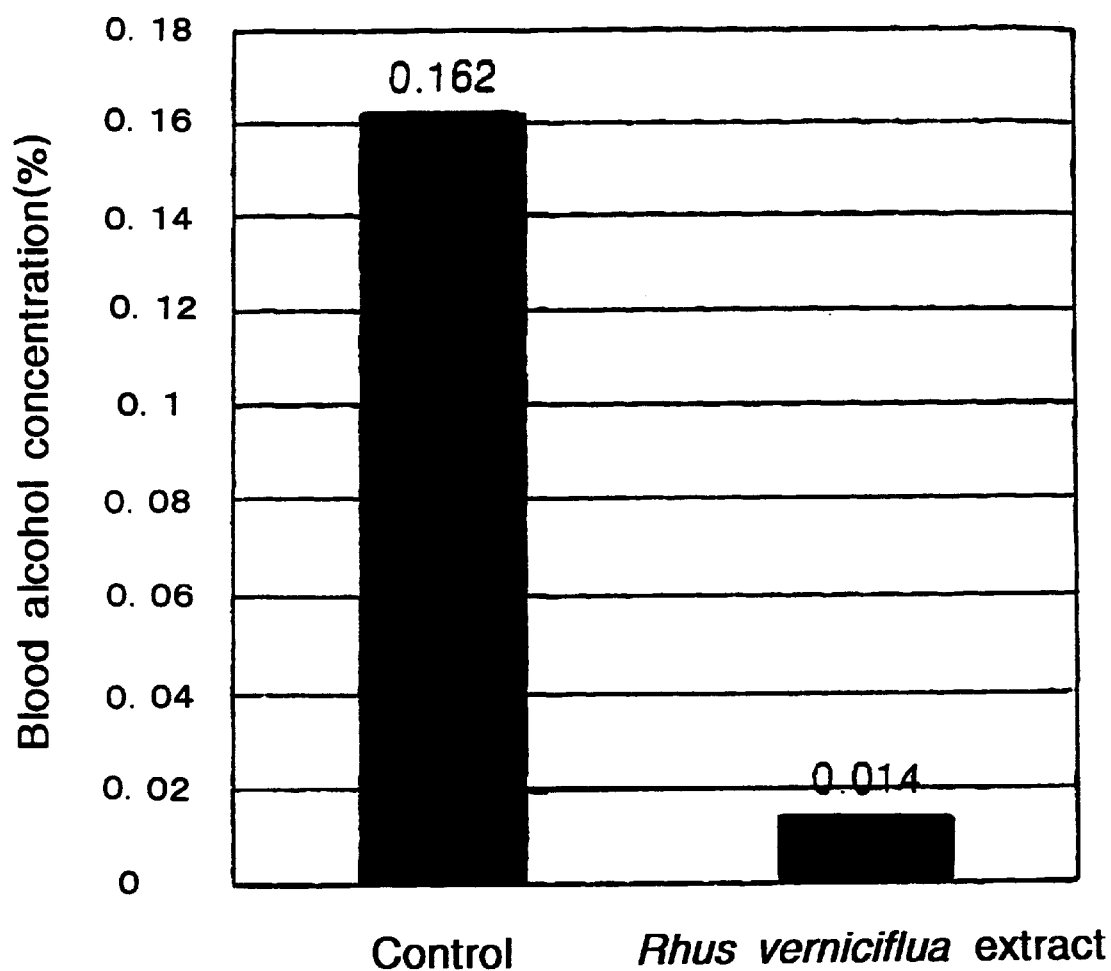
FIG. 11 displays the hangover resolving activity of the extract of *Rhus verniciflua* in comparison with that of non-treated control group.

FIG. 11 displays the hangover resolving activity of the extract of *Rhus verniciflua* in comparison to that of non-treated control group, wherein the blood alcohol concentration of the control group is 0.162% and that of test group is 0.014%. Accordingly, it has been confirmed that the extract of *Rhus verniciflua* lowers the blood alcohol concentration to a level which is only 10% of the untreated state.

EXAMPLE 8

Acute Toxicity of the Extract of *Rhus verniciflua*

4-week old specific pathogen free(SPF) Sprague-Dawley rats were acclimated for 1 week in an environmental safety cabinet(FLUFLANGCE) and healthy rats were selected for the test. The rats were divided by a group of 5 rats and put into a polycarbonate breeding case(26×42×18 cm) which was maintained at 23±3° C., relative humidity of 50±10%, ventilation of 10–20 times/hour, light period of 12 hour, and luminous intensity of 300–500 Lux. The rats were allowed free access to sterilized laboratory animal food(Shinchon Feed, Korea) and water.

Before the test, the rats were put on a 18-hour fast. They were then orally administered once with 20 ml/kg of the suspensions prepared by dissolving 5.0, 3.3, 2.2, 1.5 and 1.0 g/kg of the extract of *Rhus verniciflua* in 0.5% sodium carboxymethyl cellulose. Thereafter, the lethality of the rats were observed for 14 days.

The result in Table 6 shows that the extract of *Rhus verniciflua* does not show acute toxicity at a dose of 2.2 g/kg and below.

TABLE 6

| Dose (g/kg) | # of dead rats/# of tested rats |
|---|---|
| 1.0 | 0/5 |
| 1.5 | 0/5 |
| 2.2 | 0/5 |
| 3.3 | 5/5 |
| 5.0 | 5/5 |

While the invention has been described with respect to the above specific embodiments, it should be recognized that various modifications and changes may be made to the invention by those skilled in the art which also fall within the scope of the invention as defined by the appended claims.

What is claimed is:

1. A process for preparing an extract of *Rhus verniciflua*, which comprises:

(a) adding 0.3 to 1 l of an acetone-based solvent to 100 g of *Rhus verniciflua*, (b) allowing the mixture to stand at 20 to 60° C. for 1 to 30 days to obtain a crude extract, (c) adding water to the crude extract and filtering the resulting mixture to obtain a filtrate, (d) subjecting the filtrate to silica gel adsorption chromatography employing as an eluent a mixture of chloroform and methanol having a mixing ratio ranging from 9:1 to 7:3(v/v) to obtain the extract of *Rhus verniciflua*.

2. The process of claim 1, wherein said acetone-based solvent in step (a) has an acetone content of 90% or more.

3. A method for treating a patient suffering from a cancer comprising administering an effective amount of the extract of *Rhus Verniciflua* prepared by the process of claim 1 to the patient, said cancer being sensitive to the extract and selected from the group consisting of lung cancer, uterine cancer, skin cancer, colon cancer and central nervous system cancer.

* * * * *